(12) United States Patent
Okada et al.

(10) Patent No.: US 9,138,419 B2
(45) Date of Patent: Sep. 22, 2015

(54) PATCH PREPARATION

(75) Inventors: Yasuaki Okada, Osaka (JP); Katsuhiro Okada, Osaka (JP); Masato Nishimura, Osaka (JP); Yuji Kawaharada, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 0 days.

(21) Appl. No.: 13/983,134

(22) PCT Filed: Feb. 1, 2012

(86) PCT No.: PCT/JP2012/052306
§ 371 (c)(1),
(2), (4) Date: Aug. 1, 2013

(87) PCT Pub. No.: WO2012/105618
PCT Pub. Date: Aug. 9, 2012

(65) Prior Publication Data
US 2013/0315976 A1    Nov. 28, 2013

(30) Foreign Application Priority Data
Feb. 2, 2011  (JP) .................................. 2011021201

(51) Int. Cl.
*A61K 9/70* (2006.01)
*A61K 31/167* (2006.01)
*A61K 31/4453* (2006.01)
*A61K 31/496* (2006.01)

(52) U.S. Cl.
CPC ............. *A61K 9/7038* (2013.01); *A61K 9/7061* (2013.01); *A61K 31/167* (2013.01); *A61K 31/4453* (2013.01); *A61K 31/496* (2013.01)

(58) Field of Classification Search
CPC ... A61K 9/7061; A61K 9/7038; A61K 31/19; A61K 31/496
See application file for complete search history.

(56) References Cited

U.S. PATENT DOCUMENTS

| 2006/0093654 A1 | 5/2006 | Shirai |
| 2006/0093656 A1 | 5/2006 | Muta et al. |
| 2007/0148217 A1* | 6/2007 | Mori et al. ..................... 424/449 |
| 2007/0219286 A1* | 9/2007 | Ishii .............................. 523/111 |
| 2007/0231591 A1* | 10/2007 | Tsuru et al. ................... 428/497 |
| 2009/0169605 A1* | 7/2009 | Maeda et al. ................. 424/448 |

FOREIGN PATENT DOCUMENTS

| CN | 1717226 A | 1/2006 |
| CN | 1015100570 A | 8/2009 |
| EP | 1 568 365 | 8/2005 |
| EP | 1 757 309 | 2/2007 |
| EP | 2 036 559 | 3/2009 |
| JP | 55-017354 | 2/1980 |
| JP | 63-290819 | 11/1988 |
| JP | 6-319793 | 11/1994 |
| JP | 2001-348329 | 12/2001 |
| JP | 2003-116908 | 4/2003 |
| JP | 2004123662 A * | 4/2004 |
| JP | 2007-16019 | 1/2007 |
| JP | 2010-13470 | 1/2010 |
| WO | 2005/046680 | 5/2005 |
| WO | 2005/105060 | 11/2005 |
| WO | 2005/105150 | 11/2005 |
| WO | 2007/142295 | 12/2007 |

OTHER PUBLICATIONS

WebMD "EDTA" (http://www.webmd.com/vitamins-supplements/ingredientmono-1032-edta.aspx?activeingredientid=1032&activeingredientname=edta) accessed Dec. 17, 2014.*
Becker et al. "Safety Assessment of Silica and Related Cosmetic Ingredients" Cosmetic Ingredient Review, Sep. 25, 2009, 1-81.*
Neusilin (http://www.neusilin.com/product) accessed Dec. 23, 2014.*
JP 2004123662 Machine translation with human translation of the table. Dec. 18, 2014.*
International Search Report issued Apr. 3, 2012 in International (PCT) Application No. PCT/JP2012/052306.
Extended European Search Report issued Jun. 6, 2014 in European Application No. EP 12 74 2140.
Japanese Office Action mailed on May 19, 2015 in corresponding Japanese Application No. 020281/2012 and translation thereof.
Office Action issued Sep. 5, 2014 in corresponding Chinese Application No. 201280007477.1 with English translation.
Chinese Office Action issued May 21, 2015, in corresponding Chinese Application No. 201280007477.1 (with English translation).

* cited by examiner

*Primary Examiner* — Sean Basquill
*Assistant Examiner* — Andrew S Rosenthal
(74) *Attorney, Agent, or Firm* — Wenderoth, Lind & Ponack, L.L.P.

(57) ABSTRACT

The problem of the present invention is to provide a patch preparation containing a drug (excluding 2-(4-ethyl-1-piperazinyl)-4-(4-fluorophenyl)-5,6,7,8,9,10-hexahydrocyclooctа[b]pyridine and a physiologically acceptable acid addition salt thereof), which is superior in both the skin permeability of a drug, and adhesiveness in the presence of water.

A patch preparation containing a support and an adhesive layer on one surface of the support, wherein the adhesive layer contains a drug excluding 2-(4-ethyl-1-piperazinyl)-4-(4-fluorophenyl)-5,6,7,8,9,10-hexahydrocyclooctа[b]pyridine and a physiologically acceptable acid addition salt thereof, an acrylic polymer, lactic acid and magnesium aluminometasilicate.

12 Claims, No Drawings

PATCH PREPARATION

TECHNICAL FIELD

The present invention relates to a patch preparation to be used by adhering to a skin surface or mucosal surface.

BACKGROUND ART

In an attempt to mitigate skin irritation by an adhesive, a patch preparation having an adhesive layer added with a liquid component compatible with the adhesive is conventionally known. However, a patch preparation containing an adhesive added with such liquid component easily causes problems such as transfer of a liquid component to an adherend (skin and mucous membrane to be an adhesion target) or a support, and the like, depending on the object of use. Thus, for example, patent document 1 describes, as an adhesive for dealing with such problems, an adhesive layer wherein 40-80 wt % of the adhesive is insolubilized by crosslinking, and teaches that said adhesive layer shows improved cohesive force while having an appropriate adhesive force. However, even such an adhesive layer may be associated with a problem of decreased adhesiveness of the adhesive layer in the presence of a sweat component due to sweating. Patent document 2 describes an adhesive which avoids the aforementioned problem by adding metal chloride to the adhesive layer and prevents a decrease in the cohesive force of the adhesive layer even in the presence of a sweat component due to sweating. However, it does not consider imparting a sufficient adhesive force to an adhesive layer, and such adhesive layer had a room for further improvement.

DOCUMENT LIST

Patent Documents patent document 1: JP-A-H6-319793
patent document 2: JP-A-2007-16019

SUMMARY OF THE INVENTION

Problems to be Solved by the Invention

In view of the above-mentioned situation, the problem to be solved by the present invention is provision of a patch preparation sufficiently enhanced in not only the cohesive force of an adhesive layer and skin permeability of a drug, but also adhesiveness in the presence of water.

Means of Solving the Problems

The present inventors have conducted intensive studies in an attempt to solve the aforementioned problems and found that the above-mentioned problem can be solved by adding lactic acid and magnesium aluminometasilicate to an adhesive layer, which resulted in the completion of the present invention.

Accordingly, the present invention provides the following.
[1] A patch preparation comprising a support and an adhesive layer on one surface of the support, wherein the adhesive layer contains a drug excluding 2-(4-ethyl-1-piperazinyl)-4-(4-fluorophenyl)-5,6,7,8,9,10-hexahydrocycloocta[b]pyridine and a physiologically acceptable acid addition salt thereof, an acrylic polymer, lactic acid and magnesium aluminometasilicate.
[2] The patch preparation of the above-mentioned [1], wherein the content of the lactic acid in the adhesive layer is 0.1-10 wt % of the total weight of the adhesive layer.
[3] The patch preparation of the above-mentioned [1] or [2], wherein the adhesive layer contains 0.03-7 parts by weight of magnesium aluminometasilicate per 1 part by weight of lactic acid.
[4] The patch preparation of any one of the above-mentioned [1]-[3], wherein the magnesium aluminometasilicate is an amorphous composite oxide wherein aluminum, magnesium and a silicon atom are three-dimensionally polymerized via an oxygen atom.
[5] The patch preparation of any one of the above-mentioned [1]-[4], wherein the drug excluding 2-(4-ethyl-1-piperazinyl)-4-(4-fluorophenyl)-5,6,7,8,9,10-hexahydrocycloocta[b]pyridine and a physiologically acceptable acid addition salt thereof is a basic drug.

Effect of the Invention

The patch preparation of the present invention can enhance a skin permeation effect of a drug, since the adhesive layer contains the drug and lactic acid. While conventional preparations of this kind containing lactic acid tend to easily detach, since adhesiveness decreases in the presence of water, the patch preparation of the present invention can suppress a decrease in the adhesiveness of the patch preparation in the presence of water, and can suppress detachment from the skin and the like, since the adhesive layer further contains magnesium aluminometasilicate. Therefore, the present invention can provide a patch preparation superior in both the skin permeability of a drug, and adhesiveness in the presence of water.

DESCRIPTION OF EMBODIMENTS

The present invention is explained in the following by referring to preferable embodiments thereof.

The patch preparation of the present invention contains a drug, an acrylic polymer, lactic acid and magnesium aluminometasilicate in an adhesive layer.

The drug to be contained in the patch preparation of the present invention is not particularly limited as long as 2-(4-ethyl-1-piperazinyl)-4-(4-fluorophenyl)-5,6,7,8,9,10-hexahydrocycloocta[b]pyridine (generic name "blonanserin") and a physiologically acceptable acid addition salt thereof are excluded, and a transdermally absorbable drug, which can be administered to mammals such as human and the like through the skin, is preferable. Specific examples of such drug include general anesthetics, hypnotic sedatives, antiepileptic drugs, antipyretic analgesic antiphlogistic drugs, anti-vertiginous drugs, psychoneurotic drugs, central neurological drug, antidementia, local anesthetics, skeletal muscle relaxants, autonomic drugs, antispasmodic drugs, anti-parkinson drugs, anti-histamine drugs, cardiac stimulants, drugs for arrhythmia, diuretic, hypotensive drug, vasoconstrictor, coronary vasodilator, peripheral vasodilators, arteriosclerosis drugs, drugs for circulatory organ, anapnoics, antitussive expectorant, hormone drugs, external drugs for purulent diseases, analgesic-antipruritic-styptic-antiinflammatory drugs, drugs for parasitic skin diseases, hemostatic drugs, gout treatment drugs, drugs for diabetes, anti-malignant tumor agents, antibiotic, chemical therapy agents, narcotic, quit smoking aids and the like.

The drug includes not only drugs in the form of a free base, but also physiologically acceptable salts thereof. While such salt is not particularly limited, examples thereof include, but are not limited to, formate, acetate, lactate, adipate, citrate, tartrate, methanesulfonate, fumarate, maleate and the like, and examples of acid addition salts with inorganic acid include hydrochloride, sulfate, nitrate, phosphate and the like. In the present invention, the drug may be a solvate, a hydrate or a non-hydrate.

The present invention is particularly advantageous when the drug reacts with a highly reactive crosslinking agent (e.g., isocyanate, metal salt, epoxide-based etc.) during the crosslinking treatment of the adhesive layer to cause denaturation of the crosslinking agent and the drug itself. Examples of such drug include drugs having one or more functional groups selected from the group consisting of an alcoholic hydroxyl group, a thiol group, a phenolic hydroxyl group, and an amino group (e.g., primary (—$NH_2$), secondary (—NRH), tertiary (—NRR')).

The present invention is particularly advantageous when the drug is a basic drug having a basic group. Examples of such drug include drugs having one or more functional groups selected from the group consisting of an alcoholic hydroxyl group, a thiol group, a phenolic hydroxyl group, and an amino group (e.g., primary (—$NH_2$), secondary (—NRH), tertiary (—NRR')). In the present invention, lactic acid which is an acidic additive is added to the adhesive layer. When a basic drug and an acidic additive are co-present in an adhesive layer, a salt produced from the basic drug and the acidic additive may be transferred to the interface between the adhesive layer and the skin and act as a surfactant, whereby the patch preparation may be detached in water. However, when magnesium aluminometasilicate is added to the adhesive layer, the salt is maintained by magnesium aluminometasilicate and transfer thereof to the interface between the adhesive layer and the skin can be prevented.

In the patch preparation of the present invention, the drug is preferably a solid drug. The solid drug here means a drug which is solid at room temperature (25° C.), that is, a drug having a melting point of not less than 25° C. The melting point here is a value according to differential scanning calorimetry (DSC). As compared to liquid drugs that tend to resist release from an adhesive layer since they adsorb to magnesium aluminometasilicate, a solid drug is particularly advantageous in the present invention since it does not show such tendency. In addition, a solid drug does not easily bleed from the adhesive layer during preservation of the patch preparation.

The drug is present in the adhesive layer in an amount sufficient to provide desired results in the treatment of disease, condition or disorder, for example, desired therapeutic effect, which is referred to as an effective amount in the present specification. The effective amount of the drug means, for example, an amount of the drug that provides a concentration of the drug in blood lower than a toxic level and sufficient to provide a selected effect over a predetermined time. Such amount can be determined with ease by those of ordinary skill in the art. While the effective amount varies depending on the area of the patch preparation, it is preferably not less than 0.1 wt %, more preferably not less than 0.5 wt %, particularly preferably not less than 0.8 wt %, relative to the total weight of the adhesive layer. Since an is excessive amount may exert an adverse influence on the property of the adhesive layer, it is preferably not more than about 50 wt %, more preferably not more than about 40 wt %, particularly preferably not more than about 30 wt %.

The lactic acid contained in the adhesive layer may be any as long as it is generally used in the technical field. It may be DL-lactic acid which is a racemate, or L-lactic acid or D-lactic acid which is an optically active substance. From the aspect of easy availability, DL-lactic acid is preferable. Particularly, from the aspect of flowability, DL-lactic acid is preferable. While the content of the lactic acid in the adhesive layer can be appropriately determined and is not particularly limited, it is preferably 0.1-10 wt % of the total weight of the adhesive layer. When it is less than 0.1 wt %, an effective amount of the drug may not be transferred into the blood. When it exceeds 10 wt %, the cohesive force of the adhesive layer may decrease. In consideration of the influence on the skin irritation, lactic acid is more preferably used at not more than 6 wt %, further preferably not more than 5 wt %.

Magnesium aluminometasilicate is available under the trade name of, for example, Neusilin from Fuji Chemical Industry. In addition, magnesium aluminometasilicate is preferably an amorphous composite oxide of aluminum, magnesium and silicon atom, which are three-dimensionally polymerized via an oxygen atom. Such composite oxide is more specifically magnesium aluminometasilicate represented by the formula: $Al_2O_3/aMgO/bSiO_2.nH_2O$ wherein a=0.3-3 and b=0.3-5. Due to its porous structure, such magnesium aluminometasilicate is considered to act more advantageously when the adhesiveness in the presence of water is improved.

While the content of magnesium aluminometasilicate in the adhesive layer can be appropriately set and is not particularly limited, it is preferably 0.03-7 parts by weight relative to 1 part by weight of lactic acid in the adhesive layer. When it is less than 0.03 part by weight, the patch preparation may detach in water. When it exceeds 7 parts by weight, sufficient adhesiveness may not be afforded. The content of magnesium aluminometasilicate is more preferably 0.03-5 parts by weight in consideration of sufficient maintenance of the adhesive force to the skin.

The present invention contains an acrylic polymer as an adhesive in the adhesive layer. Preferably, the adhesive is preferably constituted by an acrylic polymer alone. When an adhesive polymer other than an acrylic polymer is contained as the adhesive, the adhesive polymer other than an acrylic polymer is contained in not more than 10 wt % relative to the total weight of the adhesive in the adhesive layer (acrylic polymer is 90 wt % or more). Examples of the adhesive polymer other than an acrylic polymer include rubber adhesive polymers, silicone adhesive polymers and the like.

The acrylic polymer in the present invention is preferably an acrylic polymer containing an alkyl(meth)acrylate unit as the main component (main constituting unit). The acrylic polymer containing an alkyl(meth)acrylate unit as the main component (main constituting unit) is preferably a copolymer of alkyl(meth)acrylate as the main component (first monomer component) and a vinyl monomer having a functional group capable of being involved in a crosslinking reaction (second monomer component), and a copolymer wherein other monomer (third monomer component) is further polymerized is particularly preferable in view of adhesiveness to human skin and dissolution property of the drug during the production of a preparation.

Examples of the above-mentioned alkyl(meth)acrylate (the first monomer component) include alkyl(meth)acrylate wherein the alkyl group is a linear, branched chain or cyclic alkyl group having a carbon number of 1 to 18 (e.g., methyl, ethyl, n-propyl, isopropyl, n-butyl, isobutyl, tert-butyl, sec-butyl, n-pentyl, isopentyl, neopentyl, n-hexyl, isohexyl, cyclohexyl, 3-methylpentyl, n-heptyl, cycloheptyl, n-octyl, 2-ethylhexyl, cyclooctyl, n-nonyl, cyclononyl, n-decyl, cyclodecyl, n-undecyl, n-dodecyl, n-tridecyl and the like) and the like, preferably alkyl(meth)acrylate wherein the alkyl group is a linear, branched chain or cyclic alkyl group having a carbon number of 4 to 18 (e.g., n-butyl, isobutyl, tert-butyl, sec-butyl, n-pentyl, isopentyl, neopentyl, n-hexyl, isohexyl, cyclohexyl, 3-methylpentyl, n-heptyl, cycloheptyl, n-octyl, 2-ethylhexyl, cyclooctyl, n-nonyl, cyclononyl, n-decyl, cyclodecyl, n-undecyl, n-dodecyl, n-tridecyl and the like). To particularly confer adhesiveness at ambient temperature, use of a monomer component that decreases the glass transition temperature of the polymer is preferable. Thus, alkyl(meth) acrylate wherein the alkyl group is a linear, branched chain or cyclic alkyl group having a carbon number of 4 to 8 (e.g., n-butyl, isobutyl, tert-butyl, sec-butyl, n-pentyl, isopentyl, neopentyl, n-hexyl, isohexyl, cyclohexyl, 3-methylpentyl, n-heptyl, cycloheptyl, n-octyl, 2-ethylhexyl, cyclooctyl and the like) is more preferable, and alkyl(meth)acrylate wherein the alkyl group is n-butyl, 2-ethylhexyl or cyclohexyl is particularly preferable.

Particularly preferable specific examples of alkyl(meth) acrylate (first monomer component) include butyl acrylate, 2-ethylhexyl acrylate, 2-ethylhexyl methacrylate, cyclohexyl acrylate, cyclohexyl methacrylate, and 2-ethylhexyl acrylate is most preferable. These alkyl(meth)acrylates (first monomer component) may be used alone or in combination of two or more kinds thereof.

In the above-mentioned vinyl monomer having a functional group capable of being involved in a crosslinking reaction (the second monomer component), examples of the functional group capable of being involved in a crosslinking reaction include a hydroxy group, a carboxyl group, a vinyl group and the like, preferably a hydroxy group and a carboxy group. Specific examples of said monomer (the second monomer component) include hydroxyethyl(meth)acrylate, hydroxypropyl(meth)acrylate, (meth)acrylic acid, itaconic acid, maleic acid, maleic anhydride, methaconic acid, citraconic acid, glutaconic acid and the like. Of these, acrylic acid, methacrylic acid and hydroxyethylacrylate are preferable, and acrylic acid is most preferable, since they are easily available. One or more kinds of these monomers (the second monomer component) can be used in combination.

In addition, the above-mentioned other monomer (the third monomer component) is mainly used for adjusting the cohesive force of the adhesive layer, adjusting solubility and releasability of a drug (compound A or a physiologically acceptable acid addition salt thereof) and the like. Examples of the monomer (the third monomer component) include vinyl esters such as vinyl acetate, vinyl propionate and the like; vinyl ethers such as methyl vinyl ether, ethyl vinyl ether and the like; vinyl amides such as N-vinyl-2-pyrrolidone, N-vinylcaprolactam and the like; alkoxy(meth)acrylates such as methoxyethyl(meth)acrylate, ethoxyethyl(meth)acrylate, tetrahydrofurfuryl(meth)acrylate and the like; hydroxy group-containing monomers such as hydroxypropyl(meth) acrylate, α-hydroxymethyl acrylate and the like; (meth) acrylic acid derivatives having an amide group such as (meth) acrylamide, dimethyl(meth)acrylamide, N-butyl(meth) acrylamide, N-methylol(meth)acrylamide and the like; aminoalkyl(meth)acrylates such as aminoethyl(meth)acrylate, dimethylaminoethyl(meth)acrylate, tert-butylaminoethyl(meth)acrylate and the like; alkoxyalkyleneglycol(meth) acrylates such as methoxyethyleneglycol(meth)acrylate, methoxydiethyleneglycol(meth)acrylate, methoxypolyethylene glycol(meth)acrylate, methoxypolypropyleneglycol (meth)acrylate and the like; (meth)acrylonitrile; sulfo group-containing monomers such as styrene sulfonic acid, ally sulfonic acid, sulfopropyl(meth)acrylate, (meth)acryloyloxynaphthalenesulfonic acid, acrylamidemethylsulfonic acid and the like; vinyl group-containing monomers such as vinyl piperidone, vinyl pyrimidine, vinyl piperazine, vinyl pyrrole, vinyl imidazole, vinyl oxazole, vinyl morpholine etc., and the like. Among these, vinyl esters and vinyl amides are preferable, vinyl ester is preferably vinyl acetate, and vinyl amide is preferably N-vinyl-2-pyrrolidone. One or more kinds of these monomers (the third monomer component) can be used in combination.

When the acrylic polymer is a copolymer of alkyl(meth) acrylate (the first monomer component) and a vinyl monomer having a functional group capable of being involved in a crosslinking reaction (the second monomer component), the copolymerization ratio (first monomer component/second monomer component) is preferably 85-99 wt %/1-15 wt %, more preferably 90-99 wt %/1-10 wt %.

When the acrylic polymer is a copolymer of alkyl(meth) acrylate (the first monomer component), a vinyl monomer having a functional group capable of being involved in a crosslinking reaction (the second monomer component), and a monomer other than these (the third monomer component), the copolymerization ratio (first monomer component/second monomer component/third monomer component) is preferably 40-94 wt %/1-15 wt %/5-50 wt %, more preferably 50-89 wt %/1-10 wt %/10-40 wt %.

While the polymerization reaction of an acrylic polymer may be performed by a method known per se and is not particularly limited, for example, a method including reacting the above-mentioned monomer in a solvent (e.g., ethyl acetate and the like) in the presence of a polymerization initiator (e.g., benzoyl peroxide, azobisisobutyronitrile and the like) at 50-70° C. for 5-48 hr can be mentioned.

The acrylic polymer in the present invention is particularly preferably a 2-ethylhexylacrylate/acrylic acid/N-vinyl-2-pyrrolidone copolymer, a 2-ethylhexylacrylate/2-hydroxyethylacrylate/vinyl acetate copolymer, a 2-ethylhexylacrylate/acrylic acid copolymer and the like, more preferably a 2-ethylhexylacrylate/acrylic acid/N-vinyl-2-pyrrolidone copolymer.

While the glass transition temperature of the acrylic polymer in the present invention also varies depending on the copolymer composition, it is generally preferably −100 to −10° C., more preferably −90 to −20° C., from the aspect of adhesiveness of a patch preparation. The glass transition temperature is a measured value by a differential scanning calorimeter.

In the patch preparation of the present invention, the content of the adhesive (adhesive polymer) in the adhesive layer is preferably 20-90 wt %, more preferably 30-80 wt %, of the total weight of the adhesive layer.

In the patch preparation of the present invention, an organic liquid component may be contained in the adhesive layer to give a soft feeling to the adhesive layer, reduce pain and irritation (physical irritation) due to the adhesive force when the adhesive patch is peeled off from the skin and the like.

Such organic liquid component can be used without any particularly limitation as long as the component itself is liquid at room temperature (25° C.), shows a plasticizing action, and is compatible with the above-mentioned acrylic polymer. The organic liquid component softens the adhesive layer, and reduces physical irritation to the skin due to the patch preparation. Specific examples of the organic liquid component include fatty acid ester (hereinafter to be also abbreviated as "C8-18 (12-16)-C1-18 fatty acid ester") such as isopropyl myristate, ethyl laurate, isopropyl palmitate, ethyl oleate, isostearyl laurate, isotridecyl myristate, octyl palmitate and the like, which is formed from a fatty acid having a carbon number of 8 to 18 (preferably 12-16) and a monohydric alcohol having a carbon number of 1 to 18; fatty acid having a carbon number of 8 to 9 [for example, caprylic acid (octanoic acid, C8), pelargonic acid (nonanoic acid, C9) and the like]; glycerin fatty acid ester (preferably, glycerol ester formed from fatty acid having a carbon number of 8-12 (may be any of monoglyceride, diglyceride and triglyceride)); glycols such as ethylene glycol, diethylene glycol, triethylene glycol, polyethylene glycol, propylene glycol, 1,3-propanediol, polypropylene glycol and the like; fats and oils such as olive oil, castor oil, squalene and the like; organic solvent such as dimethyl sulfoxide, dimethylformamide, dimethylacetamide, dimethyllauryl amide, dodecyl pyrrolidone, isosorbitol, oleyl alcohol, N-methyl-2-pyrrolidone and the like; liquid surfactant such as polyoxyethylene hydrogenated castor oil, octyl alcohol, polyethylene glycol mono-p-isooctyl phenyl ether, α-monoisostearyl glyceryl ether, lauromacrogol, lauryl alcohol, sorbitan sesquioleate, polyoxyethylene alkyl ether sodium sulfate, polyoxyethylene lauryl ether sodium sulfate, sodium alkylnaphthalenesulfonate, polyoxyethyleneoleyl amine, polyoxyethylene oleyl ether sodium phosphate, polyoxyl stearate, decaglyceryl laurate, polyoxyethylene sorbitan monolaurate, polyoxyethylene sorbitan monostearate, sorbitan monolaurate, sorbitan trioleate, polyoxyethylenesorbitol tetraoleate, glycerol monooleate, sucrose ester of fatty acid, tocopherol and the like; hydrocarbons such as liquid paraffin and the like; plasticizer to be conventionally known such as diisopropyl adipate, phthalic acid ester, diethyl sebacate and the like; lauric acid; oleic acid; ethoxylated stearyl alcohol; glycerol and the like. One kind alone or two or more kinds of these organic liquid components are used in combination. Among these, C8-18 (12-16)-C1-18 fatty acid ester is preferable, and isopropyl myristate is particularly preferable.

In the present invention, the content of the organic liquid component is preferably 5-60 wt %, more preferably 10-50 wt %, of the total weight of the adhesive layer. When the content is less than 5 wt %, the adhesive layer may not be plasticized sufficiently, a good soft feeling may not be obtained, or skin irritation may not be decreased sufficiently. Conversely, when it exceeds 60 wt %, the organic liquid component cannot be maintained in the adhesive even by the cohesive force possessed by the adhesive, it causes blooming on the surface of the adhesive layer, thus resulting in too weak adhesive force, which in turn highly possibly causes falling off of the preparation from the skin surface during use.

In the patch preparation of the present invention, the adhesive layer may be crosslinked by publicly known chemical crosslinking treatment (e.g., crosslinking treatment using a crosslinking agent) or a physical crosslinking treatment (e.g., crosslinking treatment by irradiation of electron beam such as gamma ray or irradiation of ultraviolet light). Said crosslinking treatment can be performed by a means generally performed in the field. A chemical crosslinking treatment using a crosslinking agent is preferable since crosslinking treatments do not easily cause an adverse effect on a drug.

When the an adhesive layer is subjected to a chemical crosslinking treatment using a crosslinking agent, the crosslinking agent is not particularly limited so far as formation of the crosslinking structure is not suppressed by a drug, and includes peroxides (e.g., benzoyl peroxide (BPO) and the like), isocyanate compounds (e.g., multifunctional isocyanate compound), organometallic compounds (e.g., zinc zirconium, zinc alaninate, zinc acetate, zinc glycine ammonium compounds, titanium compounds and the like), metal alcoholate (e.g., tetraethyl titanate, tetraisopropyl titanate, aluminum isopropylate, aluminum sec-butyrate and the like), metal chelate compounds (e.g., dipropoxybis(acetylacetonate)titanium, tetraoctylene glycol titanium, aluminum isopropylate, ethyl acetoacetate aluminum diisopropylate, aluminum tris (ethyl acetoacetate), aluminum tris(acetylacetonate) and the like), and the like. What is called a gel-like adhesive layer, wherein an adhesive polymer in an adhesive layer containing an adhesive and an organic liquid component is crosslinked, is preferable, since it confers a soft feeling to the skin as well as has appropriate adhesiveness and cohesive force. One or more kinds of the above-mentioned crosslinking agents may be used in combination for the crosslinking treatment. Particularly, when the adhesive layer contains an isocyanate compound, a decrease in the cohesive force of the adhesive layer during adhesion of the patch preparation to the human skin can be reduced, and cohesive failure does not easily occur during detachment of the adhesive layer. Thus, an isocyanate compound is preferable. While the content of the crosslinking agent varies depending on the kind of the crosslinking agent and adhesive, it is generally 0.03-0.6 part by weight, preferably 0.05-0.4 part by weight relative to 100 parts by weight of the adhesive to be crosslinked (acrylic polymer) (that is, generally 3-60 wt %, preferably 5-40 wt %, of the total amount of the acrylic polymer).

Examples of the isocyanate compound include aliphatic diisocyanate such as tetramethylene diisocyanate, hexamethylene diisocyanate and the like, alicyclic diisocyanate such as isophorone diisocyanate, hydrogenated xylylene diisocyanate, hydrogenated toluene diisocyanate, hydrogenated diphenylmethane diisocyanate and the like, aromatic aliphatic diisocyanate such as xylylene diisocyanate and the like, aromatic diisocyanate such as tolylenediisocyanate, 4,4'-diphenylmethane diisocyanate etc., and the like. The above-mentioned isocyanate compound may be used alone, or the same or similar adhesives (polymer components) may be used in a mixture.

The chemical crosslinking treatment may be performed by, e.g., adding a crosslinking agent, followed by heating the adhesive layer at a crosslinking reaction temperature or higher and storing thereof, that is, an aging step. The heating temperature which may be chosen depending on the kind of the crosslinking agent is preferably 60-90° C., more preferably 60-80° C. A time for the heating is preferably 12-96 hours, more preferably 24-72 hours.

The thickness of the adhesive layer of the patch preparation of the present invention is preferably 20-300 μm, more preferably 30-300 μm, most preferably 50-300 μm. When the thickness is smaller than 20 μm, it may be difficult to afford a sufficient adhesiveness and to contain an effective amount of a drug. When the thickness is higher than 300 μm, the formation of the adhesive layer may be difficult (difficult coating).

In the patch preparation of the present invention, the adhesive layer is preferably a non-aqueous adhesive layer in view of the skin adhesion. The non-aqueous adhesive layer here is not necessarily limited to one completely free of water, but includes those containing a slight amount of water (e.g., less than 1 wt % of the total weight of an adhesive layer) derived from humidity in the air, skin and the like.

The patch preparation of the present invention comprises a support and an adhesive layer, and is preferably provided with a release liner. That is, the patch preparation of the present invention has a structure wherein the aforementioned adhesive layer is laminated on at least one surface of the support, and the adhesive surface (the face opposite to the face laminated on the support) of the adhesive layer is preferably protected by being covered with a release liner until immediately before use. In addition, it is also possible to apply a back coating agent of silicone type, fluorine type, wax and the like on the support and form a roll, without using a release liner.

While the support is not particularly limited, preferred is one that does not allow a drug and an organic liquid component in the adhesive layer to pass through the support and be lost from the back face, which decreases their contents (namely, a material impermeable to the organic liquid component and drug).

Specific examples include a single film of polyester (e.g., polyethylene terephthalate etc.), nylon, polyvinyl chloride, polyethylene, polypropylene, ethylene-vinyl acetate copolymer, polytetrafluoroethylene, ionomer resin and the like, a metal foil, and a laminate film wherein two or more kinds of films selected therefrom are laminated and the like. Of these, to improve adhesiveness (anchor property) of a support to an adhesive layer, it is preferable to use, as a support, a laminate film of a non-porous film made from the above-mentioned material and the following porous film, and form the adhesive layer on the porous film side. The thickness of the non-porous film is preferably 2-100 μm, more preferably 2-50 μm.

The porous film is not particularly limited as long as the anchor property to an adhesive layer is improved and, for example, paper, woven fabric, non-woven fabric (e.g., polyester non-woven fabric and the like), a single film of the above-mentioned film (e.g., polyester (e.g., polyethylene terephthalate and the like), nylon, Saran (trade name), polyethylene, polypropylene, ethylene-vinyl acetate copolymer, polyvinyl chloride, ethylene-ethyl acrylate copolymer, polytetrafluoroethylene, metal foil, and the like, and a laminate film wherein two or more kinds of films selected therefrom are laminated and the like), which is mechanically perforated, and the like can be mentioned. Particularly, paper, woven fabric and non-woven fabric (e.g., polyester (e.g., polyethylene terephthalate and the like), non-woven fabric and the like) are preferable from the aspects of flexibility of the support. For example, when the porous film is paper, woven fabric, non-woven fabric etc., the fabric weight is preferably 5-30 g/m$^2$ to improve anchor property.

The laminate film as a support is produced by a known production method of a laminate film such as dry lamination method, wet lamination method, extrusion lamination method, hot melt lamination method, coextrusion lamination method and the like.

The thickness of the support is not particularly limited but preferably 2-200 μm, more preferably 10-50 μm. When it is less than 2 μm, the handling property such as self-supporting property may become worse. When the thickness is more than 200 the followability may become worse to cause skin discomfort.

The release liner is not particularly limited, and a known release liner can be used. Specific examples thereof include a release liner wherein a release treating agent layer comprised of the release treating agent is formed on the surface of a substrate for a release liner, a plastic film having high releasability by itself, a release liner having a constitution wherein a release layer comprised of the aforementioned plastic film material having high releasability is formed on the surface of a substrate for a release liner and the like. The release surface of the release liner may be only one surface or both surfaces of the substrate.

In such release liner, the release treating agent is not particularly limited and, for example, release agents such as a long chain alkyl group-containing polymer, a silicone polymer (silicone release agent), a fluorine polymer (fluorine release agent) and the like can be mentioned. Examples of the substrate for a release liner include plastic films such as a PET film, a polyimide film, a polypropylene film, a polyethylene film, a polycarbonate film, a polyester (excluding PET) film and the like, and metallized plastic films wherein a metal is evaporated on these films; papers such as Japanese paper, Western paper, craft paper, glassine paper, fine paper and the like; a substrate made of a fibrous material such as non-woven fabric, cloth and the like; a metal foil and the like.

As the plastic film having high releasability by itself, polyethylene (low density polyethylene, linear low density polyethylene etc.), polypropylene, ethylene-α-olefin copolymers (block copolymer or random copolymer) such as ethylene-propylene copolymer and the like, a polyolefin film made of a polyolefin resin comprised of a mixture of these; Teflon (registered trade mark) film and the like can be used.

The release layer formed on the surface of the aforementioned substrate for a release liner can be formed by laminating or coating the aforementioned plastic film material having high releasability on the aforementioned substrate for a release liner.

The thickness of the release liner is not particularly limited but is normally 200 μm or less, preferably 25-100 μm.

While the production method of the patch preparation of the present invention is not particularly limited, it can be produced by, for example, the following production method. First, an adhesive polymer, a drug and a filler are added, together with an organic liquid component and other additives as necessary, to a suitable solvent and the mixture is sufficiently mixed until it becomes homogeneous. Examples of the solvent include ethyl acetate, toluene, hexane, 2-propanol, methanol, ethanol and the like. When a crosslinking agent is added, it is added to the mixture and the mixture is sufficiently mixed. Where necessary, a solvent may be added along with a crosslinking agent and they are mixed.

Then, the obtained mixture is applied to one surface of the support or a release treating surface of the release liner, and dried to form an adhesive layer. The aforementioned application can be performed by, for example, casting, printing and other techniques known per se to those of ordinary skill in the art. Thereafter, a release liner or support is adhered to the adhesive layer to form a laminate. When a crosslinking treatment is performed, the release liner or support is adhered to the adhesive layer, and they are left standing at 60-90° C., preferably 60-70° C., for 24-48 hr to promote the crosslinking reaction, whereby a crosslinked adhesive layer is formed.

Then, the release liner is peeled off, the exposed surface of the adhesive layer is immersed a lactic acid solution wherein lactic acid is dissolved in a solvent, and dried at about 40-100° C. After drying, a release-treated surface of a release liner different from the above is adhered to the adhesive layer.

EXAMPLES

The present invention is explained in more detail in the following by referring to Examples, which are not to be construed as limitative. In the following, "parts" and "%" mean "parts by weight" and "wt %", respectively, unless particularly specified.

[Preparation of Acrylic Polymer A]

Under an inert gas atmosphere, 2-ethylhexylacrylate (75 parts), N-vinyl-2-pyrrolidone (22 parts), acrylic acid (3 parts) and azobisisobutyronitrile (0.2 part) were subjected to solution polymerization in ethyl acetate at 60° C. to give an acrylic copolymer (acrylic polymer A) solution.

Example 1

To acrylic polymer A (58.01 parts), lidocain (hereinafter to be referred to as "LDC") (5.82 parts), isopropyl myristate (hereinafter to be referred to as "IPM") (32.98 parts) and magnesium aluminometasilicate (Neusilin (trade name), type: UFL2, manufactured by Fuji Chemical Industry) (0.1 part) was added a moderate amount of ethyl acetate and the solution was sufficiently mixed until it became homogeneous. As a crosslinking agent, trifunctional isocyanate (CORONATE HL (manufactured by Japan Polyurethane Industry), 0.09 part) was added. The concentration of the base was adjusted to 30 wt % with ethyl acetate and the mixture was sufficiently mixed and stirred until it became homogeneous to give a coating solution. The obtained coating solution was applied to a release-treated surface of a release liner, which was a 75 μm-thick polyethylene terephthalate (hereinafter "PET") film subjected to a release treatment with a silicone release agent, such that the thickness of the adhesive layer after drying was about 60 μm, and dried to form an adhesive layer. The adhesive surface of the adhesive layer thus formed was adhered to a nonwoven fabric side of a laminate support of a 3.5 μm-thick PET film and a PET nonwoven fabric with a fabric weight of 12 g/m$^2$ to give a laminate. The laminate was left standing at 70° C. for 48 hr to prepare a laminate having a crosslinked adhesive layer. After standing, the release liner of the laminate having a crosslinked adhesive layer was detached, the crosslinked adhesive layer was immersed in lactic acid such that the final content of lactic acid was 3 parts relative to the crosslinked adhesive layer (97 parts). Thereafter, a release liner which was the same as the above-mentioned release liner was separately prepared, and adhered to the adhesive surface of the crosslinked adhesive layer to give a patch preparation of Example 1. The melting point of lidocain is 66-69° C. The melting point was measured by a DSC apparatus (manufactured by Seiko Instruments Inc. (SII), model number DSC6220). The above-mentioned base concentration refers to a value (wt %) obtained by subtracting the weight of ethyl acetate from the weight (g) of the coating solution, dividing the obtained value by the weight (g) of the coating solution and multiplying the obtained value by 100.

Example 2

In the same manner as in Example 1 except that acrylic polymer A (56.61 parts) and Neusilin (1.5 parts) were used instead, the patch preparation of Example 2 was obtained.

Example 3

In the same manner as in Example 1 except that acrylic polymer A (55.22 parts), Neusilin (2.9 parts), and a crosslinking agent (0.08 part) were used instead, the patch preparation of Example 3 was obtained.

Example 4

In the same manner as in Example 1 except that acrylic polymer A (53.72 parts), Neusilin (4.4 parts), and a crosslinking agent (0.08 part) were used instead, the patch preparation of Example 4 was obtained.

Example 5

In the same manner as in Example 1 except that acrylic polymer A (47.93 parts), Neusilin (10.2 parts), and a crosslinking agent (0.07 part) were used instead, the patch preparation of Example 5 was obtained.

Example 6

In the same manner as in Example 1 except that acrylic polymer A (43.53 parts), Neusilin (14.6 parts), and a crosslinking agent (0.07 part) were used instead, the patch preparation of Example 6 was obtained.

Example 7

In the same manner as in Example 1 except that acrylic polymer A (38.74 parts), Neusilin (19.4 parts), and a crosslinking agent (0.06 part) were used instead, the patch preparation of Example 7 was obtained.

Comparative Example 1

In the same manner as in Example 1 except that acrylic polymer A (58.11 parts) and Neusilin (0.0 part) were used instead, the patch preparation of Comparative Example 1 was obtained.

Example 8

To acrylic polymer A (58.01 parts), Biperiden. (hereinafter to be referred to as "BPD") (5.82 parts), IPM (32.98 parts), and magnesium aluminometasilicate (Neusilin (trade name) (0.1 part) was added a moderate amount of ethyl acetate and the solution was sufficiently mixed until it became homogeneous. As a crosslinking agent, trifunctional isocyanate (CORONATE HL (manufactured by Japan Polyurethane Industry), 0.09 part) was added. The concentration of the base was adjusted to 30 wt % with ethyl acetate and the mixture was sufficiently mixed and stirred until it became homogeneous to give a coating solution. The obtained coating solution was applied to the release-treated one surface of a release liner, which was a 75 μm-thick polyethylene terephthalate (hereinafter "PET") film subjected to a release treatment with a silicone release agent, such that the thickness of the adhesive layer after drying was 60 μm, and dried to form an adhesive layer. The adhesive surface of the adhesive layer thus formed was adhered to a nonwoven fabric side of a laminate film of a 3.5 μm-thick PET film and a PET nonwoven fabric at 12 g/m$^2$ to give a laminate. The laminate was left standing at 70° C. for 48 hr to prepare a laminate having a crosslinked adhesive layer. After standing, the release liner of the laminate having a crosslinked adhesive layer was detached, the crosslinked adhesive layer was immersed in lactic acid such that the final content of lactic acid was 3 parts relative to the crosslinked adhesive layer (97 parts). Thereafter, a release liner which was the same as the above-mentioned release liner was separately prepared, and adhered to the adhesive surface of the crosslinked adhesive layer to give a patch preparation of Example 8. The above-mentioned base concentration refers to a value (wt %) obtained by subtracting the weight of ethyl acetate from the weight (g) of the coating solution, dividing the obtained value by the weight (g) of the coating solution and multiplying the obtained value by 100.

Example 9

In the same manner as in Example 8 except that acrylic polymer A (56.61 parts) and Neusilin (1.5 parts) were used is instead, the patch preparation of Example 9 was obtained.

Example 10

In the same manner as in Example 8 except that acrylic polymer A (55.22 parts), Neusilin (2.9 parts), and a crosslinking agent (0.08 part) were used instead, the patch preparation of Example 10 was obtained.

Example 11

In the same manner as in Example 8 except that acrylic polymer A (53.72 parts), Neusilin (4.4 parts), and a crosslinking agent (0.08 part) were used instead, the patch preparation of Example 11 was obtained.

Example 12

In the same manner as in Example 8 except that acrylic polymer A (47.93 parts), Neusilin (10.2 parts), and a crosslinking agent (0.07 part) were used instead, the patch preparation of Example 12 was obtained.

Example 13

In the same manner as in Example 8 except that acrylic polymer A (43.53 parts), Neusilin (14.6 parts), and a crosslinking agent (0.07 part) were used instead, the patch preparation of Example 13 was obtained.

Example 14

In the same manner as in Example 8 except that acrylic polymer A (38.74 parts), Neusilin (19.4 parts), and a crosslinking agent (0.06 part) were used instead, the patch preparation of Example 14 was obtained.

Comparative Example 2

In the same manner as in Example 8 except that acrylic polymer A (58.11 parts), and Neusilin (0.0 part) were used instead, the patch preparation of Comparative Example 2 was obtained.

[Adhesive Force Measurement Test]

A sample cut into width 24 mm, length 50 mm was press-adhered to a stainless board by one reciprocation of a 2 kg roller and, after 30 min, the sample was peeled off at a peel angle 180°, rate 300 mm/min and the release force at that time was measured. The test was performed with n=3, the load at 3 points was measured for each test and the 9 points in total were averaged. The test points were 20, 40, 60 mm from the detaching start position. The results are shown in Table 1 and Table 2.

[Holding Power Measurement Test]

A sample is cut in 10 mm, length 50 mm and one end (about 25 mm) thereof is pressed against a bakelite (phenol resin) plate by one reciprocation of a roller (weight 850 g). The other end is reinforced with an auxiliary sheet. This is set on a hook in an apparatus stabilized at a temperature of 40±2° C., left for 30 min, attached with a load (300 g) and left until natural falling occurs. The retention time then was measured. The experiment was performed at n=3, and the total 3 measured values were averaged. The results thereof are shown in Table 1 and Table 2.

[Constant Load Peeling Test]

A sample is cut in 12 mm, length 50 mm and one end (about 5 mm) is peeled off and reinforced with an auxiliary sheet. The test piece is pressed against a bakelite (phenol resin) plate by one reciprocation of a roller (weight 850 g). After 30 min, the test piece is peeled off from the plate until the length of the adhered part of the test piece is 30 mm. The test piece was placed horizontally on a test table in a water bath at 40±2° C., a 30 g load was set on the auxiliary sheet, and the time necessary for the test piece to naturally fall from the test plate was measured and the peeling rate (mm/min) of the preparation in the presence of water was determined. When the test piece does not fall after lapse of 30 min, the peeling length at the time point of 30 min is measured by a ruler and divided by 30 to give the peeling rate. The experiment was performed at n=3, and the total 3 points were averaged. The results thereof are shown in Table 1 and Table 2.

[Anchor Property]

Whether the adhesive layer was anchoring on the support side when the liner was peeled off from the patch preparation (liner peeling operation) was evaluated by visual observation. Furthermore, the patch preparation was adhered to a phenol resin plate, and whether the adhesive layer was anchoring on the support side when the patch preparation was detached was evaluated by visual observation (adhesion test). The anchor property was evaluated according to the following criteria. The evaluation results are shown in Table 1 and Table 2.

◯: The adhesive layer was anchoring on the support in both liner peeling operation and adhesion test.

Δ: The adhesive layer was anchoring on the support in liner peeling operation but was not in adhesion test.

x: The adhesive layer was not anchoring on the support in liner peeling operation.

[Stickiness]

The liner was peeled off, and sensory evaluation of the stickiness when the exposed adhesive layer was touched by finger was performed according to the following criteria. The evaluation results are shown in Table 1 and Table 2.

◯: Stickiness was sufficient.

Δ: Stickiness was rather weak.

x: Stickiness was weak.

TABLE 1

| | LDC (%) | acrylic polymer A (%) | IPM (%) | lactic acid (%) | magnesium alumino-meta-silicate (Neusilin) (%) | crosslinking agent relative to adhesive layer (%) | crosslinking agent relative to adhesive (%) | adhesive force (N/24 mm) | holding power (min) | constant load peeling (peeling rate) (mm/min) | stickiness | anchor property |
|---|---|---|---|---|---|---|---|---|---|---|---|---|
| Ex. 1 | 5.82 | 58.01 | 32.98 | 3 | 0.1 | 0.09 | 0.15 | 1.908 | 6.6 | 0.39 | ◯ | ◯ |
| Ex. 2 | 5.82 | 56.61 | 32.98 | 3 | 1.5 | 0.09 | 0.15 | 1.702 | 2.1 | 0.11 | ◯ | ◯ |
| Ex. 3 | 5.82 | 55.22 | 32.98 | 3 | 2.9 | 0.08 | 0.15 | 1.817 | 1.4 | 0.09 | ◯ | ◯ |
| Ex. 4 | 5.82 | 53.72 | 32.98 | 3 | 4.4 | 0.08 | 0.15 | 1.699 | 1.3 | 0.07 | ◯ | ◯ |
| Ex. 5 | 5.82 | 47.93 | 32.98 | 3 | 10.2 | 0.07 | 0.15 | 1.673 | 3.1 | 0.04 | ◯ | ◯ |
| Ex. 6 | 5.82 | 43.53 | 32.98 | 3 | 14.6 | 0.07 | 0.15 | 1.686 | 6.3 | 0.07 | ◯ | ◯ |
| Ex. 7 | 5.82 | 38.74 | 32.98 | 3 | 19.4 | 0.06 | 0.15 | 0.948 | 5.9 | 0.59 | ◯ | Δ |
| Comp. Ex. 1 | 5.82 | 58.11 | 32.98 | 3 | 0 | 0.09 | 0.15 | 1.737 | 2.2 | 0.6 | ◯ | ◯ |

TABLE 2

| | BPD (%) | acrylic polymer A (%) | IPM (%) | lactic acid (%) | magnesium alumino-metasilicate (Neusilin) (%) | crosslinking agent relative to adhesive layer (%) | crosslinking agent relative to adhesive (%) | adhesive force (N/24 mm) | holding power (min) | constant load peeling (peeling rate) (mm/min) | sticki-ness | anchor property |
|---|---|---|---|---|---|---|---|---|---|---|---|---|
| Ex. 8 | 5.82 | 58.01 | 32.98 | 3 | 0.1 | 0.09 | 0.15 | 1.855 | 2.9 | 0.89 | ○ | ○ |
| Ex. 9 | 5.82 | 56.61 | 32.98 | 3 | 1.5 | 0.09 | 0.15 | 1.802 | 2.9 | 0.54 | ○ | ○ |
| Ex. 10 | 5.82 | 55.22 | 32.98 | 3 | 2.9 | 0.08 | 0.15 | 1.781 | 2.5 | 0.23 | ○ | ○ |
| Ex. 11 | 5.82 | 53.72 | 32.98 | 3 | 4.4 | 0.08 | 0.15 | 1.755 | 3.8 | 0.06 | ○ | ○ |
| Ex. 12 | 5.82 | 47.93 | 32.98 | 3 | 10.2 | 0.07 | 0.15 | 1.326 | 6.5 | 0.03 | ○ | ○ |
| Ex. 13 | 5.82 | 43.53 | 32.98 | 3 | 14.6 | 0.07 | 0.15 | 1.454 | 6.6 | 0.04 | ○ | ○ |
| Ex. 14 | 5.82 | 38.74 | 32.98 | 3 | 19.4 | 0.06 | 0.15 | 0.702 | 6.2 | 0.74 | ○ | x |
| Comp. Ex. 2 | 5.82 | 58.11 | 32.98 | 3 | 0 | 0.09 | 0.15 | 1.782 | 3.4 | 1.3 | ○ | ○ |

As compared to Comparative Example 1 and Comparison 2, the peeling rate was slow in water in Examples 1-7 and Examples 8-14, it was confirmed that the preparation containing magnesium aluminometasilicate was superior in adhesiveness in water.

INDUSTRIAL APPLICABILITY

The patch preparation of the present invention can enhance a skin permeation effect of a drug, since the adhesive layer contains the drug and lactic acid. While conventional preparations of this kind containing lactic acid tend to easily detach, since adhesiveness decreases in the presence of water, the patch preparation of the present invention can suppress a decrease in the adhesiveness of the patch preparation in the presence of water, and can suppress detachment from the skin and the like, since the adhesive layer further contains magnesium aluminometasilicate. Therefore, the present invention can provide a patch preparation superior in both the skin permeability of a drug, and adhesiveness in the presence of water.

This application is based on patent application No. 2011-021201 filed in Japan, the contents of which are incorporated in full herein.

The invention claimed is:

1. A patch preparation comprising a support and a non-aqueous adhesive layer on one surface of the support, wherein the non-aqueous adhesive layer contains a drug, an acrylic polymer, lactic acid and magnesium aluminometasilicate, wherein the drug is not 2-(4-ethyl-1-piperazinyl)-4-(4-fluorophenyl)-5,6,7,8,9,10-hexahydrocycloocta[b]pyridine and a physiologically acceptable acid addition salt thereof.

2. The patch preparation according to claim 1, wherein the content of the lactic acid in the non-aqueous adhesive layer is 0.1-10 wt % of the total weight of the non-aqueous adhesive layer.

3. The patch preparation according to claim 1, wherein the non-aqueous adhesive layer contains 0.03-7 parts by weight of magnesium aluminometasilicate per 1 part by weight of lactic acid.

4. The patch preparation according to claim 1, wherein the magnesium aluminometasilicate is an amorphous composite oxide wherein aluminum, magnesium and a silicon atom are three-dimensionally polymerized via an oxygen atom.

5. The patch preparation according to claim 1, wherein the drug excluding 2-(4-ethyl-1-piperazinyl)-4-(4-fluorophenyl)-5,6,7,8,9,10-hexahydrocycloocta[b]pyridine and a physiologically acceptable acid addition salt thereof is a basic drug.

6. The patch preparation according to claim 2, wherein the non-aqueous adhesive layer contains 0.03-7 parts by weight of magnesium aluminometasilicate per 1 part by weight of lactic acid.

7. The patch preparation according to claim 2, wherein the magnesium aluminometasilicate is an amorphous composite oxide wherein aluminum, magnesium and a silicon atom are three-dimensionally polymerized via an oxygen atom.

8. The patch preparation according to claim 3, wherein the magnesium aluminometasilicate is an amorphous composite oxide wherein aluminum, magnesium and a silicon atom are three-dimensionally polymerized via an oxygen atom.

9. The patch preparation according to claim 2, wherein the drug excluding 2-(4-ethyl-1-piperazinyl)-4-(4-fluorophenyl)-5,6,7,8,9,10-hexahydrocycloocta[b]pyridine and a physiologically acceptable acid addition salt thereof is a basic drug.

10. The patch preparation according to claim 3, wherein the drug excluding 2-(4-ethyl-1-piperazinyl)-4-(4-fluorophenyl)-5,6,7,8,9,10-hexahydrocycloocta[b]pyridine and a physiologically acceptable acid addition salt thereof is a basic drug.

11. The patch preparation according to claim 4, wherein the drug excluding 2-(4-ethyl-1-piperazinyl)-4-(4-fluorophenyl)-5,6,7,8,9,10-hexahydrocycloocta[b]pyridine and a physiologically acceptable acid addition salt thereof is a basic drug.

12. The patch preparation according to claim 1, wherein the acrylic polymer is a copolymer of an alkyl(meth)acrylate and a vinyl monomer having a functional group capable of being involved in a crosslinking reaction, or a copolymer of an alkyl(meth)acrylate and a vinyl monomer having a functional group capable of being involved in a crosslinking reaction further comprising a third monomer, and wherein the third monomer is one kind of monomer selected from the group consisting of vinyl esters, vinyl ethers, vinyl amides, alkoxy (meth)acrylates, hydroxy group-containing monomers, (meth)acrylic acid derivatives having an amide group, aminoalkyl(meth)acrylates, alkoxyalkyleneglycol(meth)acrylates, (meth)acrylonitrile, sulfo group-containing monomers, and vinyl group-containing monomers.

* * * * *